(12) United States Patent
Chung (10) Patent No.: US 12,269,850 B2
(45) Date of Patent: Apr. 8, 2025

(54) COMPOSITION FOR TREATING OR PREVENTING COLORECTAL DISEASE CONTAINING CONSTRUCT FOR EXPRESSION OF P8 PROTEIN DERIVED FROM LACTIC ACID BACTERIA

(71) Applicant: CELL BIOTECH CO., LTD., Gyeonggi-do (KP)

(72) Inventor: Myung Jun Chung, Seoul (KP)

(73) Assignee: CELL BIOTECH CO., LTD., Gyeonggi-Do (KR)

( * ) Notice: Subject to any disclaimer, the term of this patent is extended or adjusted under 35 U.S.C. 154(b) by 62 days.

(21) Appl. No.: 15/734,107

(22) PCT Filed: Aug. 6, 2020

(86) PCT No.: PCT/KR2020/010432
§ 371 (c)(1),
(2) Date: Dec. 1, 2020

(87) PCT Pub. No.: WO2021/049764
PCT Pub. Date: Mar. 18, 2021

(65) Prior Publication Data
US 2023/0183301 A1   Jun. 15, 2023

(30) Foreign Application Priority Data
Sep. 11, 2019  (KR) ................ 10-2019-0112682

(51) Int. Cl.
*C07K 14/335*   (2006.01)
*A61P 1/00*     (2006.01)
(Continued)

(52) U.S. Cl.
CPC .............. *C07K 14/335* (2013.01); *A61P 1/00* (2018.01); *A61P 35/00* (2018.01); *C12N 15/09* (2013.01);
(Continued)

(58) Field of Classification Search
CPC ............ A61P 1/00; A61P 35/00; C12N 15/85; C12N 2800/107; C12N 2800/22; C07K 14/335
See application file for complete search history.

(56) References Cited

FOREIGN PATENT DOCUMENTS

| JP | 2004511248 A | 4/2004 |
|----|--------------|--------|
| JP | 2006254919 A | 9/2006 |

(Continued)

OTHER PUBLICATIONS

English translation of Japanese Office Action issued in connection with corresponding JP Application No. 2020-567088 dated Jan. 11, 2022 (Year: 2022).*

(Continued)

*Primary Examiner* — Gary B Nickol
*Assistant Examiner* — Amelia Nicole Dickens
(74) *Attorney, Agent, or Firm* — Tarolli, Sundheim, Covell & Tummino LLP (57) ABSTRACT

The present disclosure relates to a construct for expression of P8 protein derived from lactic acid bacteria, and a composition for treating or preventing colorectal disease containing the same. The P8 protein expression construct of the present disclosure may endogenously express P8 protein in cancer cells, thereby significantly enhancing the anticancer effect of the P8 protein through cell-cycle arrest activity.

4 Claims, 12 Drawing Sheets

Specification includes a Sequence Listing.

(51) Int. Cl.
    *A61P 35/00*     (2006.01)
    *C12N 15/09*     (2006.01)
    *C12N 15/70*     (2006.01)
    *C12N 15/85*     (2006.01)
    *A61K 38/00*     (2006.01)

(52) U.S. Cl.
    CPC ............ *C12N 15/70* (2013.01); *C12N 15/85* (2013.01); *A61K 38/00* (2013.01); *C07K 2319/21* (2013.01); *C07K 2319/50* (2013.01); *C12N 2800/107* (2013.01); *C12N 2800/22* (2013.01)

(56) References Cited

FOREIGN PATENT DOCUMENTS

| | | | |
|---|---|---|---|
| JP | 2019519221 A | 7/2019 | |
| JP | 2019141088 A | 8/2019 | |
| KR | 20180060228 A | 6/2018 | |
| KR | 1020180087662 A | 8/2018 | |
| KR | 101915951 B1 | 11/2018 | |
| WO | WO-2018097402 A1 * | 5/2018 | ............. A23L 33/18 |
| WO | 2019139229 A1 | 7/2019 | |

OTHER PUBLICATIONS

An et al. "Colorectal Cancer Therapy Using a Pediococcus pentosaceus SL4 Drug Delivery System Secreting Lactic Acid Bacteria-Derived Protein p8", Nov. 11, 2019, Molecules and Cells, 42(11), p. 755-762. (Year: 2019).*

Gamallat et al. "Lactobacillus rhamnosus induced epithelial cell apoptosis, ameliorates inflammation and prevents colon cancer development in an animal model", 2016, Biomedicine & Pharmacotherapy, vol. 83, p. 536-541. (Year: 2016).*

English translation of WO 2018097402 A1. (Year: 2018).*

An et al. "Anti-Colorectal Cancer Effects of Probiotic-Derived p8 Protein", Aug. 19, 2019, Genes, vol. 10, Article 624, p. 1-12. (Year: 2019).*

Inouye et al. "Codon optimization of genes for efficient protein expression in mammalian cells by selection of only preferred human codons", Feb. 7, 2015, Protein Expression and Purification, vol. 109, p. 47-54. (Year: 2015).*

Valacco et al. "Cell Growth-Dependent Subcellular Localization of p8", 2006, Journal of Cellular Biochemistry, vol. 97, p. 1066-1079. (Year: 2006).*

Japanese Office Action issued in connection with corresponding JP Application No. 2020-567088 dated Jan. 11, 2022.

International Search Report for PCT/KR2020/010432 dated Dec. 30, 2020.

Feng, et al. "Lactobacillus rhamnosus strain LR-B1 chromosome, complete genome", Submitted (Dec. 16, 2017) Zhejiang University School of Medicine, Zhejiang University School of Medicine, 866 Yuhangtang Road, Hangzhou, Zhejiang 310058, China, GenBank Accession No. CP025428.1.

An, et al. "Anti-Colorectal Cancer Effects of Probiotic-Derived p8 Protein" , Genes 2019, 10, 624; doi:10.3390/genes10080624, Aug. 19, 2019.

* cited by examiner

COMPOSITION FOR TREATING OR PREVENTING COLORECTAL DISEASE CONTAINING CONSTRUCT FOR EXPRESSION OF P8 PROTEIN DERIVED FROM LACTIC ACID BACTERIA

TECHNICAL FIELD

The present disclosure relates to a construct for expression of P8 protein derived from lactic acid bacteria, and a composition for treating or preventing colorectal disease containing the same.

BACKGROUND ART

In 2018, in the United States, about 145,600 adults were diagnosed with colorectal cancer, and about 51,020 people died of colorectal cancer. The 5-year survival rate of colorectal cancer in the United States is about 65%. Colorectal cancer is a cancer that can invade or spread to other parts of the body. Treatments of colorectal cancer include a combination of surgery, radiotherapy, chemotherapy, and targeted therapy. Chemotherapy for colorectal cancer involves natural, synthetic, or biological substances that suppress or prevent progression. However, many chemotherapy agents are toxic to normal cells.

To identify new biotherapeutic drugs having no severe side effects, many studies have been conducted on probiotics. Because human intestinal microbes and probiotics are generally regarded as safe, proteins isolated from probiotics may have anti-colorectal cancer effects but may show reduced systemic toxicity. Indeed, a probiotic-derived protein that suppresses colorectal cancer has few adverse effects (Widakowich, C. et al., A. Review: Side effects of approved molecular targeted therapies in solid cancers. Oncologist 2007, 12, 1443-1455; Steidler, L.; Vandenbroucke, K. Genetically modified *Lactococcus lactis*: Novel tools for drug delivery. Int. J. Dairy Technol. 2006, 59, 140-146). Generally, food-grade bacteria are safe to ingest. Historically, such microbes have not been associated with the development of sinister pathologies. Indeed, their positive impact on health is well documented in the context of human and animal food production. Thus, it can be concluded that probiotic-derived proteins are relatively safe.

To identify novel therapeutic proteins against colorectal cancer, probiotics were selected in the laboratory (An, B. C.; Ryu, Y.; Yoon, Y.-S.; Choi, O.; Park, H. J.; Kim, T. Y.; Chung, M. J. Colorectal cancer therapy using a *Pediococcus pentosaceus* SL4 drug delivery system secreting lactic acid bacteria-derived protein p8. Moll. Cells under review). In this screening process, an 8-kDa protein (hereinafter referred to as "P8 protein") isolated from *Lactobacillus rhamnosus* (LR) KCTC 12202BP was identified, and this protein was found to suppress growth of colorectal cancer cells. DLD-1 cells were used to find that the P8 protein suppresses tumor growth and has anti-proliferative and anti-migration activities. However, these anti-cancer activities were quite weak because the P8 protein did not penetrate cells efficiently. Therefore, there is a need for new therapies to improve the delivery of the P8 protein into cells.

The patent documents and references mentioned in the present specification are incorporated herein by reference to the same extent as if each reference is individually and clearly specified by reference.

DISCLOSURE

Technical Problem

The present inventors have made extensive research efforts to develop a novel drug delivery system capable of enhancing the anticancer activity of P8 protein. As a result, the present inventors have developed a gene expression construct capable of stably expressing P8 protein in mammalian cells, and have experimentally found that, when the developed P8 protein expression construct is successfully expressed in colorectal cancer cells, the anticancer effect of the P8 protein against the colorectal cancer cells may be enhanced, thereby completing the present disclosure.

Therefore, an object of the present disclosure is to provide a P8 protein expression construct including: (a) a promoter; and (b) a P8 protein-encoding nucleotide sequence operatively linked to the promoter.

Another object of the present disclosure is to provide a pharmaceutical composition for treating or preventing colorectal disease, the pharmaceutical composition containing: (a) a therapeutically effective amount of a P8 protein expression construct including a P8 protein-encoding nucleotide sequence operatively linked to a promoter; and (b) a pharmaceutically acceptable carrier.

Other objects and technical features of the present disclosure will be disclosed in more detail with reference to the following description of the disclosure, the appended claims and the accompanying drawings.

Technical Solution

In accordance with one aspect of the present disclosure, the present disclosure provides a P8 protein expression construct including: (a) a promoter; and (b) a P8 protein-encoding nucleotide sequence operatively linked to the promoter.

The present disclosure is directed to an expression system for enhancing the anti-cancer activity of "P8 protein" by endogenously expressing the P8 protein in mammalian cells, preferably mammalian cancer cells.

In the present disclosure, "P8 protein" is a 8-kDa protein isolated from *Lactobacillus Rhamnosus* (LR) KCTC 12202BP by the present inventors, and was found to have excellent anticancer activity.

In the present disclosure, the P8 protein-encoding nucleotide sequence is a codon-optimized sequence for expression in eukaryotic cells.

According to one embodiment of the present disclosure, the P8 protein-encoding nucleotide sequence is the nucleotide sequence of SEQ ID NO: 3.

As used herein, the term "expression construct" refers to an essential element for expression including a nucleotide sequence to be expressed and an expression sequence (e.g., a promoter) for inducing the expression of the nucleotide sequence. Preferably, the expression construct may include a transcription regulatory sequence, a nucleotide sequence to be expressed, and a polyadenylation sequence.

As used herein, the term "promoter" refers to a DNA sequence capable of regulating expression of a protein- or nucleic acid molecule-encoding nucleotide sequence or a functional RNA. More preferably, the term "promoter" as used herein refers to a transcription regulatory sequence capable of inducing transcription of a gene (polynucleotide sequence) to be expressed in eukaryotic cells. Examples of the promoter sequence operable in eukaryotic cells include, but are not limited to, cytomegalovirus immediate early promoter, SV40 promoter (SV40 late promoter and SV40 early promoter), herpes simplex virus (HSV) tk promoter, adenovirus 2 major late promoter (PAdmI), adenovirus 2 early promoter (PAdE2), human parvovirus-associated virus (AAV) p19 promoter, Epstein-Barr virus (EBV) promoter, Rous sarcoma virus (RSV) promoter, Vaccinia virus 7.5K promoter, mouse metallothionein (MT) promoter, MMTV LTR promoter, HIV LTR promoter, β-actin promoter, EF1 alpha promoter, human IL-2 gene promoter, human IFN gene promoter, human IL-4 gene promoter, human lymphotoxin gene promoter, human GM-CSF gene promoter, and human hemoglobin-, human muscle creatine- or human metallothionein-derived promoter.

As used herein, the term "operatively linked" refers to a functional linkage between a nucleic acid expression regulatory sequence (e.g., promoter sequence) and another nucleotide sequence, whereby the regulatory sequence regulates transcription and/or translation of the other nucleotide sequence.

The expression construct of the present disclosure may include a polyadenylation sequence as a transcription termination sequence, and examples of the polyadenylation sequence include, but are not limited to, bovine growth hormone terminator (Gimmi, E. R., et al., *Nucleic Acids Res.* 17: 6983-6998 (1989)), SV40-derived polyadenylation sequence (Schek, N, et al., *Mol. Cell Biol.* 12: 5386-5393 (1992)), HIV-1 polyA (Klasens, B. I. F., et al., *Nucleic Acids Res.* 26: 1870-1876 (1998)), β-globin polyA (Gil, A., et al, *Cell* 49: 399-406 (1987)), HSV TK polyA (Cole, C. N. and T. P. Stacy, *Mol. Cell. Biol.* 5: 2104-2113 (1985)), or polyomavirus polyA (Batt, D. B and G. G. Carmichael, *Mol. Cell. Biol.* 15: 4783-4790 (1995)).

In addition, the expression construct of the present disclosure may include, as a selection marker, an antibiotic-resistant gene commonly employed in the art. For example, the expression construct may include a gene resistant to ampicillin, gentamicin, carbenicillin, chloramphenicol, streptomycin, kanamycin, geneticin (G418), neomycin or tetracycline.

The expression construct of the present disclosure may be constructed in various forms. For example, the expression construct may be constructed as a plasmid vector or viral vector system.

In accordance with another aspect of the present disclosure, the present disclosure provides a pharmaceutical composition for treating or preventing colorectal disease, the pharmaceutical composition containing: (a) a therapeutically effective amount of a P8 protein expression construct including a P8 protein-encoding nucleotide sequence operatively linked to a promoter; and (b) a pharmaceutically acceptable carrier.

The content related to "P8 protein expression construct" in the pharmaceutical composition of the present disclosure is the same as the content described above with respect to "the P8 protein expression construct including: (a) a promoter; and (b) a P8 protein-encoding nucleotide sequence operatively linked to the promoter", which is the other aspect of the present disclosure, and thus the description thereof is omitted herein.

According to one embodiment of the present disclosure, the P8 protein-encoding nucleotide sequence is the nucleotide sequence of SEQ ID NO: 3.

According to another embodiment of the present disclosure, the promoter is a promoter for expression in eukaryotic cells.

According to still another embodiment of the present disclosure, the expression construct is a plasmid vector- or viral vector-based expression construct.

As used with respect to the pharmaceutical composition of the present disclosure, the term "therapeutically effective amount" refers to an amount sufficient to achieve a therapeutic or preventive effect against colorectal disease.

As used herein, the term "pharmaceutically acceptable carrier" refers to a carrier that is commonly used for formulation. Examples of the pharmaceutically acceptable carrier include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. In addition, the composition of the present disclosure may further contain a lubricant, a wetting agent, a sweetener, a flavoring agent, an emulsifier, a suspending agent, a preservative, or the like, in addition to the above-described components.

The pharmaceutical composition of the present disclosure may be administered parenterally. For example, the pharmaceutical composition may be administered intravenously, intraperitoneally, intramuscularly, subcutaneously or topically.

A suitable dose of the pharmaceutical composition of the present disclosure may vary depending on factors such as formulation method, administration mode, the patient's age, body weight and sex, the severity of disease symptoms, diet, administration time, administration route, excretion rate, and responsivity. A physician of ordinary skill in the art can easily determine and prescribe the administration dose effective for desired treatment.

The pharmaceutical composition of the present disclosure may be provided in unit-dosage forms or multiple-dosage forms using a pharmaceutically acceptable carrier and/or excipient according to a method that may be easily carried out by those skilled in the art to which the present disclosure pertains. At this time, the formulation may be in the form of a solution in an oil or aqueous medium, a suspension, an emulsion, an extract, a powder, a granule, a tablet, or a capsule. In addition, the formulation may further contain a dispersant or a stabilizer.

In one embodiment of the present disclosure, "colorectal disease" refers to a collection of diseases that occur in the large intestine. Preferred examples of the colorectal disease include, but are not limited to, colorectal cancer, colon polyps, colitis, ischemic bowel disease, dysentery, intestinal vascular dysplasia, diverticulosis, irritable bowel syndrome, and Crohn's disease. Most preferably, the colorectal disease is colorectal cancer.

Advantageous Effects

The present disclosure relates to a construct for expression of P8 protein derived from lactic acid bacteria, and a composition for treating or preventing colorectal disease containing the same. The P8 protein expression construct of the present disclosure may endogenously express P8 protein in cancer cells, thereby significantly enhancing the anticancer effect of the P8 protein through cell-cycle arrest activity.

DESCRIPTION OF DRAWINGS

FIG. 2e shows the results of measuring the apoptotic property of exogenous P8 protein treatment. P8 protein (40 μM) was incubated with DLD-1 cells ($3\times10^3$ cells/well) for 72 hours, and then two types of cells [control and r-p8 (40 μM) treatment] were stained with the Live/Dead cell markers SYTO™ 9 (Green)/EthD-1 (red) or with the total cell marker Hoechst (blue).

BEST MODE

Specific examples described in the present specification are intended to represent exemplary embodiments or examples of the present disclosure, and the scope of the present disclosure is not limited thereby. It will be apparent to those skilled in the art that variations and other uses of the present disclosure do not depart from the scope of the present disclosure as defined in the appended claims of the present specification.

EXAMPLES

Experimental Methods

1. Bacterial Strains and Culture Thereof

P8 protein was obtained from a *Lactobacillus rhamnosus* (LR) KCTC 12202BP areain, which was isolated from the human feces. LR is a probiotic and was obtained from the culture collection maintained at Cell Biotech Co., Ltd (Gimpo, Korea). A pCI-neo expression vector was used as a delivery vehicle for endogenous expression of P8 protein. Cells were cultured for 18 to 24 hours at 37° C. in De Man, Rogosa and Sharpe agar (MRS) broth (Difco, Detroit, MI, USA). *Escherichia coli* (*E. coli*) strains DH5a and C41 (DE3) (Novagen, Madison, WI, USA) were cultured in Luria-Bertani (LB) broth (Difco) at 37° C. for 18 to 24 hours.

TABLE 1

| Target cells/Mapping | Codon-optimized sequences | Size (bp) |
|---|---|---|
| Original P8 protein | atggcaacagtagatcctga aagacattgtttctcgatg aaccaatgaacaaggtattt gactggagcaacagcgaagc acctgtacgtgatgcgctgt gggattattacatggaaaag aacagccgtgataccatcaa gactgaagaagaaatgaaac cagtcctagacatgtccgac gatgaggtcaaagccctagc agaaaaggttctcaagaagt aa (SEQ ID NO: 1) | 222 |
| *E. coli* cells/ 6XHis-TEV-P8 (NdeI/ EcoRI) | <u>catatg</u>agaggatcgcatca ccatcaccatcac-attacg atatcccaacgaccgaaaac ctgtattttcagg<u>gatcc</u>-a tggcaacagtagatcctgaa aagacattgtttctcgatga accaatgaacaaggtatttg actggagcaacagcgaagca cctgtccgtgatgcgctgtg ggattattacatggaaagaga acagccgtgatactatcaag actgaagaagaaatgaaacc agtcctagacatgtccgacg acgaggtcaaagccctagca gaaaaggttctcaagaagta <u>ggaattc</u> (SEQ ID NO: 2) | 305 |
| DLD-1 cells/ P8 (EcoRI/ NotI) | <u>gaattc</u>atggctactgtcga cccagaaaaaaccctgttct tggacgaaccaatgaataaa gtctttgattggtccaactc tgaggcccggtacgggatg cgttgtgggattactacatg gaaaaaattccagggatac cattaaaacagaagaagaaa tgaagccagttctggacatg agtgacgacgaagtgaaagc cctcgcggaaaagttctca agaaataagg<u>cggccgc</u> (SEQ ID NO: 3) | 236 |

The underlined portions in the sequences shown in Table 1 above are restriction enzyme cleavage sites.

2. Construction of Codon-Optimized His-Tagged P8 Protein, and Expression and Purification in *E. coli*

In order to express P8 protein in *E. coli* cells, the codon-optimized P8 protein gene harboring a hexa-histidine (6×His) tag and a Tobacco Etch Virus (TEV) protease cleavage site (305 bp) was synthesized by Cosmogenetech, Inc. (Seoul, Korea) (Table 1). The P8 protein was expressed using expression vector pET-28a. The P8 construct was transformed into *E. coli* strain C41 (DE3), which was cultured in M9 medium until the O.D. value reached 0.6. Overexpression of selenomethionine-substituted (SeMet) P8 protein was initiated by addition of 0.5 mM IPTG for 4 hours. Cells were harvested and then re-suspended in 20 mM HEPES (pH 7.5)/150 mM NaCl. After sonication, the cell supernatant was obtained by centrifugation. The P8 protein was purified by binding to Ni2+-NTA agarose (Qiagen, Valencia, CA), followed by washing with 20 mM HEPES (pH 7.5)/150 mM NaCl/20 mM imidazole. The 6×His tag was removed by TEV protease in the presence of 1 mM DTT. The homogeneity of the SeMet P8 protein was checked by size exclusion chromatography (HILOAD® 26/60 SUPERDEX® 200 pg (GE Healthcare) equilibrated with 20 mM HEPES (pH 7.5)/150 mM NaCl).

3. Expression of Codon-Optimized P8 Protein in DLD-1 Cells

The P8 protein gene codon for expression in mammalian cells was synthesized by Cosmogenetech, Inc. The P8 DNA fragment (236 bp) was digested with EcoRI/NotI and then cloned into the pCI-neo vector via the EcoRI/NotI site (Promega, Madison, WI) (Table 1). The resulting construct was then transformed into E. coli DH5a for amplification thereof. All restriction enzymes used were purchased from New England BioLabs (Ipswich, MA). Colorectal cancer cells (DLD-1) were transfected with plasmid DNA (pCI-neo and pCI-neo-p8). Before transfection, DLD-1 cells were plated in 6-well plates at a density of $7 \times 10^5$ cells per well. After incubating overnight, the cells were transfected using LIPOFECTAMINE™ 3000 (Invitrogen) in accordance with the manufacturer's instructions. The transfected cells were selected in RPMI 1640 medium containing antibiotics (G-418) (Sigma, St. Louis, MO, USA).

4. Cell Culture

Human colorectal cancer (CRC) cell line DLD-1 was purchased from the Korean Cell Line Bank (KCLB; Seoul, Korea) and maintained under 5% $CO_2$/37° C. in RPMI-1640 medium (Gibco, Grand Island, N.Y.) containing 10% fetal bovine serum (Gibco) and 1% penicillin/streptomycin (Gibco).

5. Cell Proliferation Assay

DLD-1 cell lines (pCI-neo (EV) and pCI-neo-P8 (P8)) were seeded in 96-well plates ($1 \times 10^3$ cells per well) and incubated at 37° C. After 72 hours, cell viability was determined by an MTT assay (Cell Counting Kit-8; Dojindo Laboratories, Tokyo, Japan). Absorbance was measured using a multifunctional microplate reader (SPECTRA-MAX™ M5; Molecular Devices, Sunnyvale, CA, USA).

6. Wound Healing Assay

DLD-1 cell lines (EV and P8) were seeded on 6-well plates ($5 \times 10^6$ cells per well). At 24 hours after seeding, the middle of the plate was scratched using a pipette tip. Then, the cells were washed three times with phosphate buffered saline (PBS) and incubated at 37° C. for 3 days. Wound healing was observed daily under a microscope (Nikon, Tokyo, Japan).

7. ELISA Analysis

The optimized ELISA procedure was performed as follows: 96-well polystyrene plates (SPL Life Sciences, Pocheon-si, Gyeonggi-do, Korea) were coated overnight at 4° C. with 100 μL diluted anti-P8 IgG (1:5500) (polyclonal-rabbit; Young In Frontier Co., Ltd, Seoul, Korea) in ELISA coating buffer (Bethyl Laboratories, Montgomery, TX, USA). Next, the wells were washed twice with 300 μL wash buffer (1× Tris-Buffered-Saline Buffer (TBS) with 0.05% Tween-20 (TBS-T)), followed by blocking with 300 μL blocking buffer (1×PBS and 5% Fetal Bovine Serum (FBS; Gibco)) for 1 hour at room temperature. Prior to addition of protein samples (nucleus extracts: 100 μL), the wells were washed three times with 300 μL wash buffer, followed by 150 min of incubation at mom temperature. After sample binding, the wells were washed four times with 300 μL wash buffer (TBS-T), followed by addition of 100 μL anti-P8 IgG-biotin (Young In Frontier Co., Ltd) in 1×PBS/ 5% FBS for 90 minutes at mom temperature. Next, the wells were washed four times with 300 μL wash buffer (TBS-T), followed by addition of 100 μL streptavidin-HRP (166 pg/mL) (Young In Frontier Co., Ltd) in 1×PBS/2.5% FBS for 30 minutes at mom temperature. Next, the wells were washed four times with 300 μL wash buffer (TBS-T), followed by color development after addition of 100 μL tetramethylbenzidine (TMB) one solution (Bethyl Laboratories; Montgomery, Tex., USA) for 20 minutes at room temperature in the dark. The reaction was stopped by addition of 50 μL stop buffer (Bethyl Laboratories). Absorbance was measured using a multifunctional microplate reader (SpectraMax SPECTRAMAX™ M5; Molecular Devices). To construct a standard curve for P8 protein, mouse sera (2-fold dilutions: 1000 ng/mL to 15.625 ng/mL) was assayed in triplicate. Each sample was assayed at two different dilutions and run in duplicate. Results for endogenous P8 protein are reported as nanograms/milliliter (ng/ mL).

8. Western Blot Analysis

DLD-1 cells were lysed in RIPA lysis buffer containing a protease inhibitor cocktail (Roche). Next, proteins (40 μg total) were separated by sodium dodecyl sulfate polyacrylamide gel electrophoresis (SDS-PAGE) and transferred to a polyvinylidene difluoride (PVDF) membrane (Amersham Bioscience, Piscataway, NJ, USA). The blotted membranes were blocked in 5% skimmed milk/T-TBS and then incubated overnight at 4° C. with appropriate primary antibodies (Cell Signaling Technology, Danvers, MA, USA); all antibodies were diluted 1:1000. The membranes were washed three times (each for 15 min) with T-TBS and then blocked with 5% skimmed milk/T-TBS. Then, the membranes were incubated with an HRP-linked secondary antibody (Cell Signaling Technology) at 4° C. for 1 hour. Glyceraldehyde 3-phosphate dehydrogenase (GAPDH) was used as an internal control. Protein bands were detected using an enhanced chemiluminescence kit (Millipore, Billerica, MA, USA), followed by autoradiography using a Chemi-Doc™ Touch Imaging System (Bio-Rad Laboratories, CA, USA).

9. Immunocytochemistry Using ImageXpress® Micro Confocal Microscopy

Colorectal cancer cells (DLD-1) were seeded onto coverslips placed in 6-well plates. After 24 hours, P8 protein (0 to 40 μM) was added to each well for additional 72 hours. Cells were fixed in 3% paraformaldehyde (PFA) at room temperature for 15 minutes and then washed three times in PBS. The cells were permeabilized by incubation in 0.2% Triton X-100/PBS for 2 min and then washed. To reduce background signals, the cells were blocked with 4% bovine serum albumin (BSA) in PBS for 30 minutes. Next, the cells were incubated with a rabbit polyclonal anti-P8 antibody (Young In Frontier Co., Ltd) overnight at 4° C. or with a mouse monoclonal anti-EpCAM antibody (Cell Signaling Technology) at 4° C. for 2 hours. Protein localization was visualized using FITC-conjugated goat anti-rabbit IgG (Jackson ImmunoResearch Laboratories, Inc.; West Grove, PA, USA) and Alexa Fluor 568-conjugated donkey anti-mouse IgG (Invitrogen). For nuclear staining, the cells were incubated with 5 μg/mL Hoechst 33,258 (Sigma) at room temperature for 1 hour, washed three times in PBS, and then mounted. Images were obtained under an ImageXpress® Micro Confocal microscope (Molecular Devices).

10. Flow Cytometry Assay

To investigate the effects of endogenous P8 protein on the cell cycle phase distribution, the cells were analyzed by flow cytometry. DLD-1 cell lines (EV and P8) were plated and incubated for 48 hours. The DLD-1 cells were removed from culture dishes by trypsinization, collected by centrifugation, and then washed with PBS. $5 \times 10^5$ cells from each sample were fixed in ice-cold 70% ethanol and incubated on ice for at least 30 minutes. Then, the cells were washed in PBS, and re-suspended in 400 μL PBS, and 50 μL RNAse (1 mg/mL) and 50 μL propidium iodide (0.4 mg/ml) were added. After incubation (at room temperature for 1 hour), the stained nuclei were analyzed with a flow cytometer (FACSCalibur, BD Biosciences, Glostrup, Denmark) Cell cycle distribution was analyzed.

Experimental Results

1. Endogenous P8 Protein Expression

Figure 1:
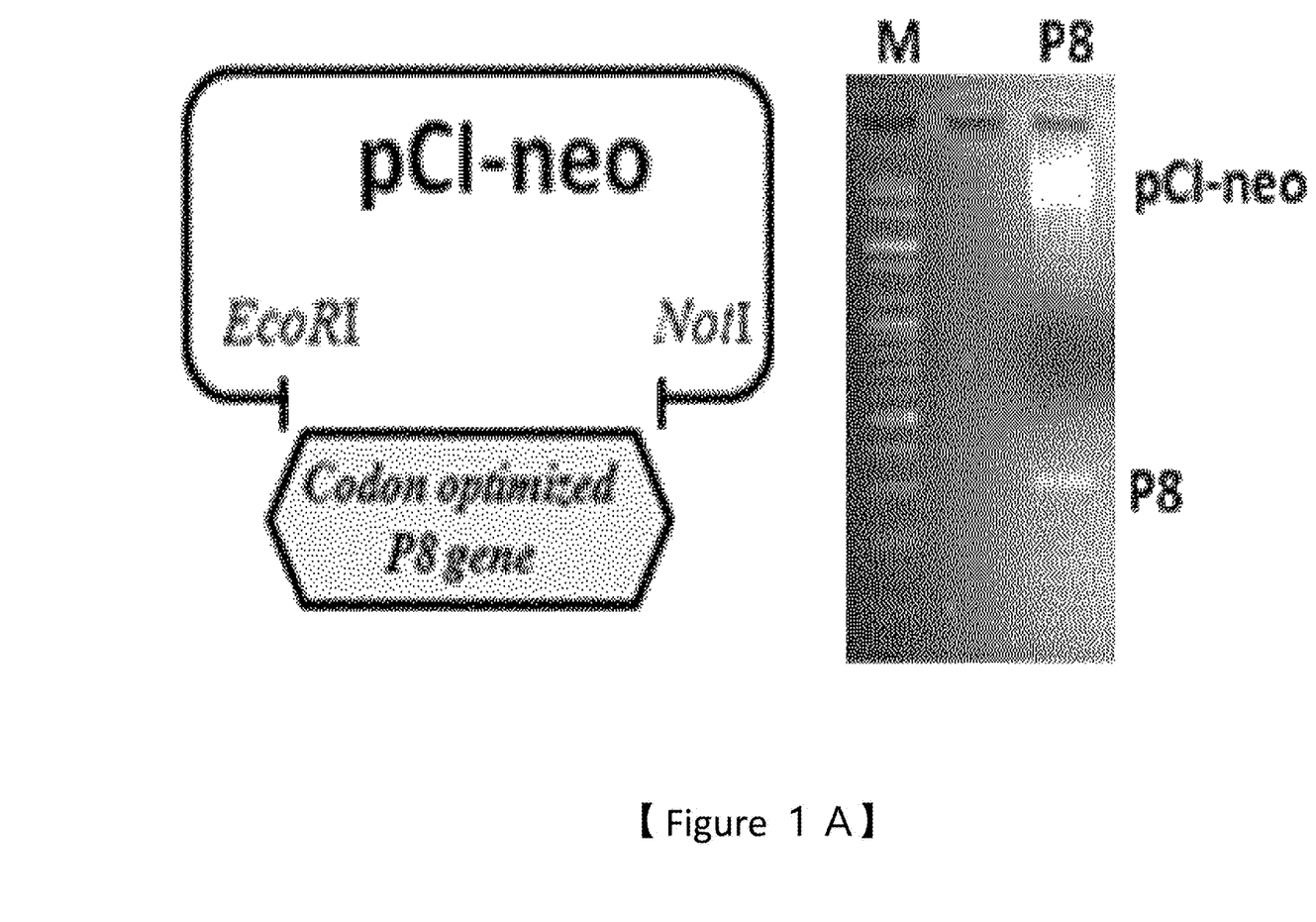
FIG. 1*a* is a schematic view showing that a codon-optimized P8 protein-encoding gene was cloned into a pCI-neo expression plasmid (EcoRI, NodI).
FIG. 1B shows the results of analyzing endogenous expression of P8 protein by Western blotting [lane 1: r-p8 (100 ng), lane 2: DLD-1 cell extract (30 μg), lane 3: EV cell line extract (30 jig), lane 4: P8 cell line extract (30 μg)]. GAPDH was used as an internal control.
FIG. 1c shows the results of observing endogenous P8 protein expression inside cells by ImageXpress® Micro Confocal microscopy (60×). The cells were stained to detect p8 (green), the cell membrane marker EpCAM (red), nuclei (DAPI: blue).
FIG. 1d shows the results of confirming endogenous expression of P8 protein in the nucleus. The upper panel shows the results of Western blotting of nuclear extracts, and the lower panel shows the results of ELISA analysis of nuclear extracts Lamin B1 was used as an internal control.
FIG. 1e shows the results of Western blotting performed to confirm that there is no cytoplasmic contamination in an isolated nuclear fraction [lane 1: DLD-1 cell lysate (30 μg), lane 2: cytoplasm fraction (30 μg), lane 3: nuclear fraction (30 μg)]. GAPDH was used as a cytoplasmic probe.
Figure 1C:
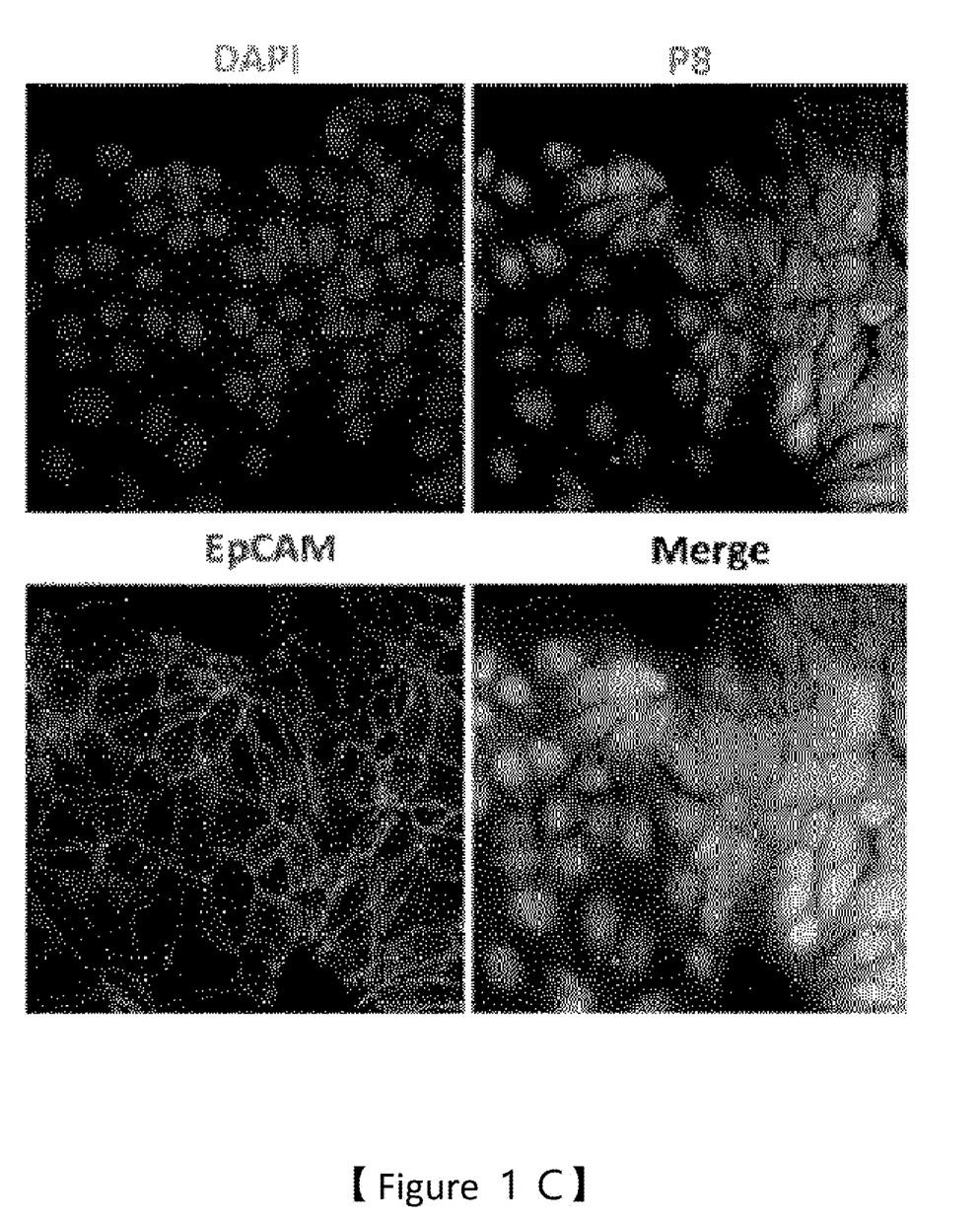
Figure 1D:
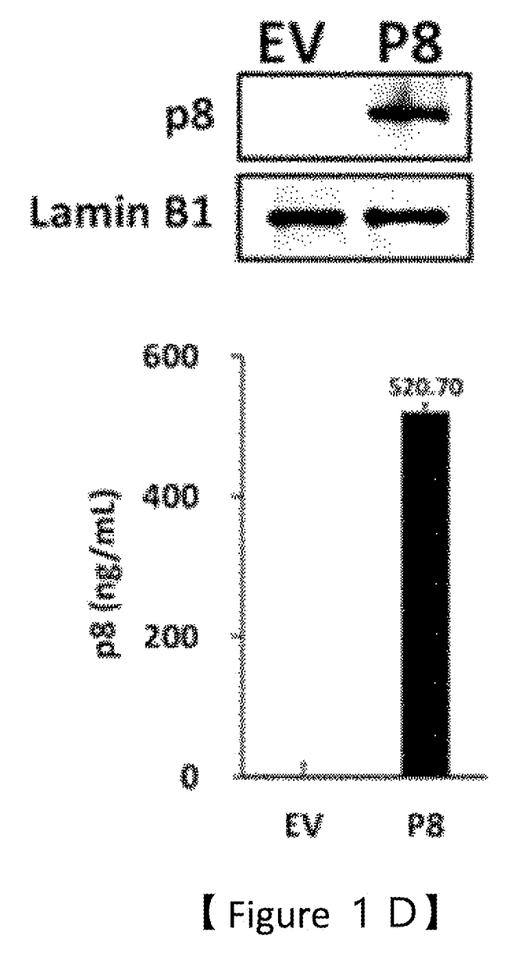

To increase the anticancer activity of P8 protein, P8 protein was endogenously expressed in mammalian cells using a codon-optimized sequence and a pCI-neo vector (FIG. 1a). Expression of endogenous P8 protein was measured by Western blotting (FIG. 1B), and intracellular localization of endogenous P8 protein was visualized using ImageXpress® Micro Confocal microscopy (FIG. 1c). The endogenously expressed P8 protein was observed in both the cytosol and nucleus (FIG. 1c). Western blotting and ELISA (lower panel) of nuclear extracts confirmed that the endogenously expressed P8 protein was translocated to the nucleus from the cytoplasm (FIGS. 1d and 1e).

2. Significant Increase in Anticancer Activity by Endogenous P8 Protein Expression To evaluate whether endogenous P8 protein expression increases its anticancer properties in vitro, the ability of P8 protein to suppress proliferation of cancer cells was measured. As a result of the experiment, endogenous P8 protein expression reduced tumor cell proliferation by about 40% (FIG. 2a), which was 2-fold greater than that by 40 μM exogenous P8 protein treatment. Moreover, endogenous P8 protein expression suppressed colony formation (FIG. 2b) and migration activities (FIG. 2c) of DLD-1 cells compared to a control. From these experimental results, it could be seen that the anticancer activity of P8 protein was dependent on the amount of the protein that entered the cells.

Figure 2:
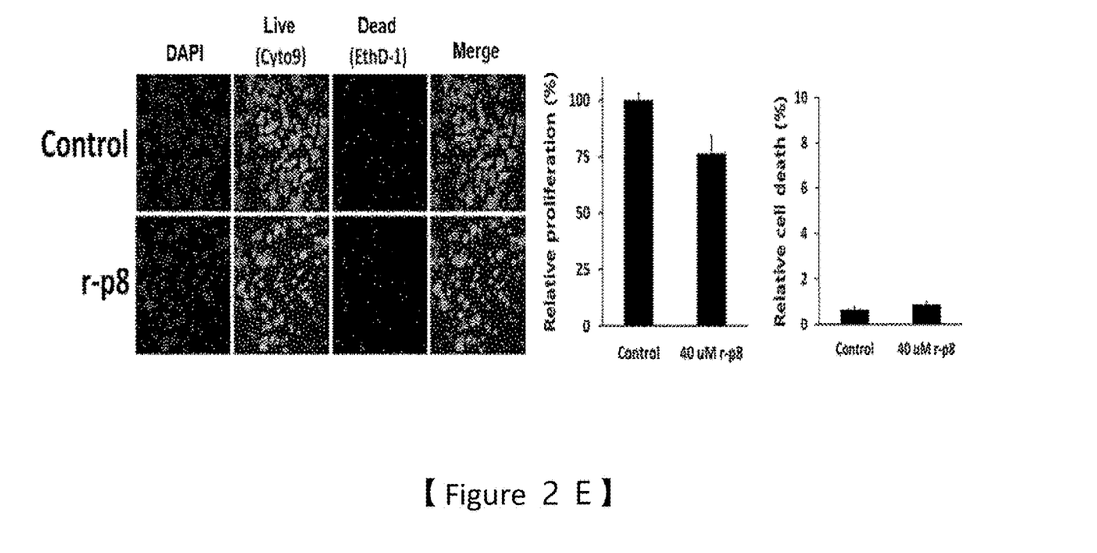
Figure 2A:
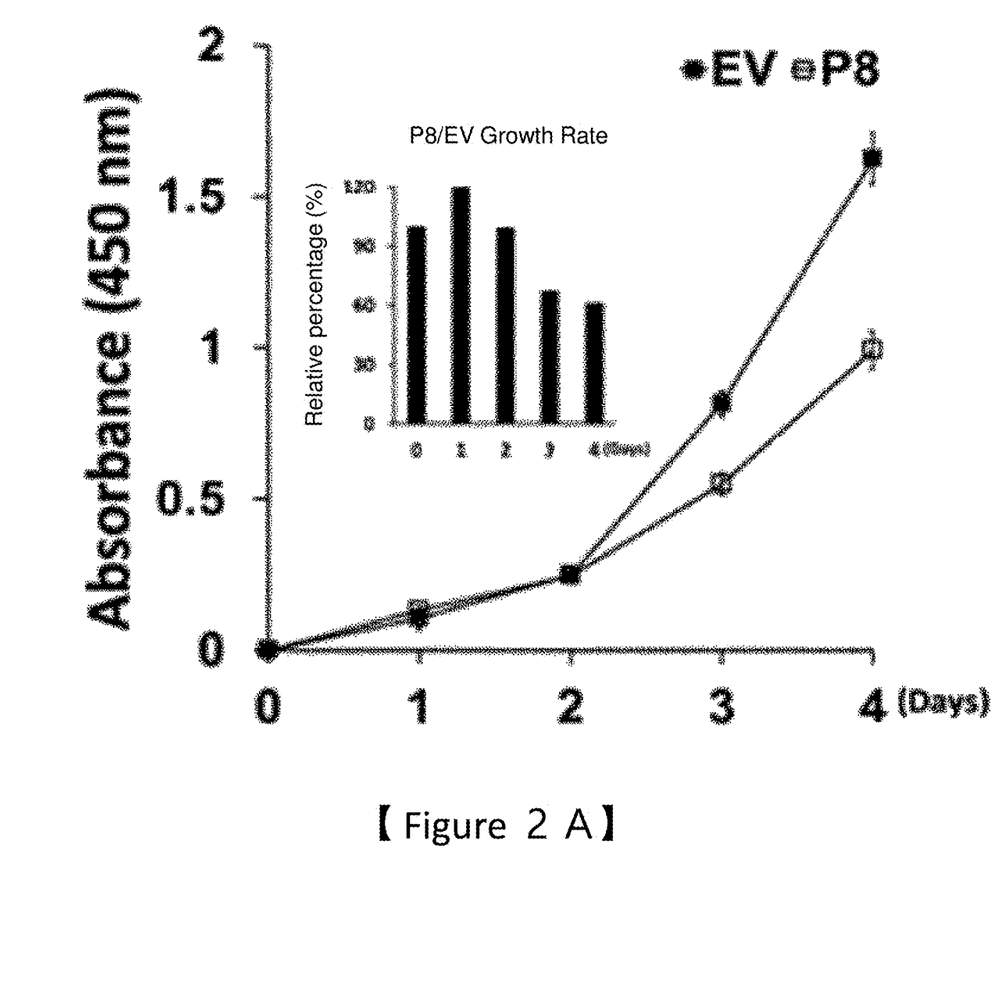
FIG. 2a shows the results of examining the anti-proliferative effects of P8 protein by an MTT assay in order to examine whether endogenous expression enhances the anti-cancer activity of endogenous P8 protein expression.
Figure 2B:
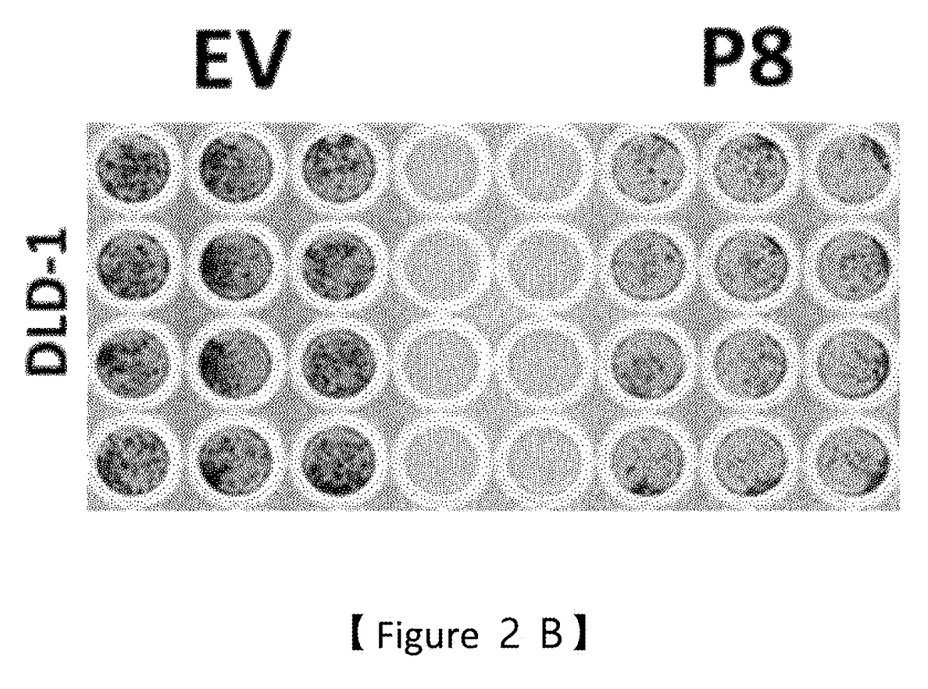
FIG. 2b shows the results of determining colony formation after endogenous expression of P8 protein that was determined by staining with crystal violet.
Figure 2C:
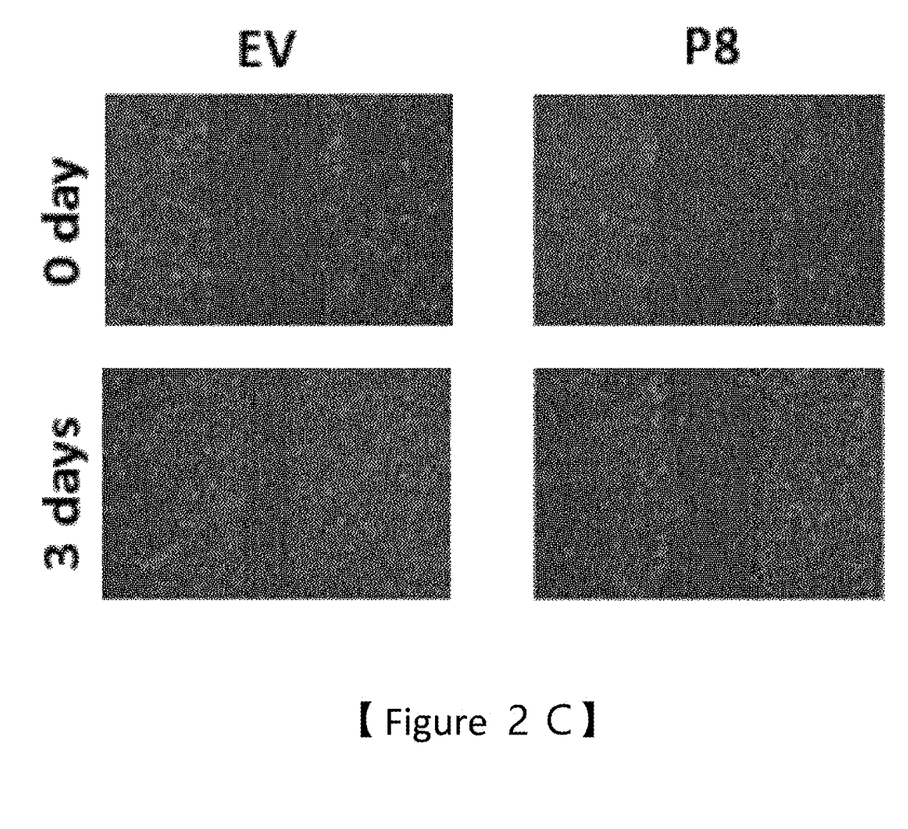
FIG. 2c shows the results of determining the anti-migration activity of endogenous expression of P8 protein. The anti-migration activity was determined by a wound healing assay. Wound recovery was analyzed using Image J.
Figure 2D:
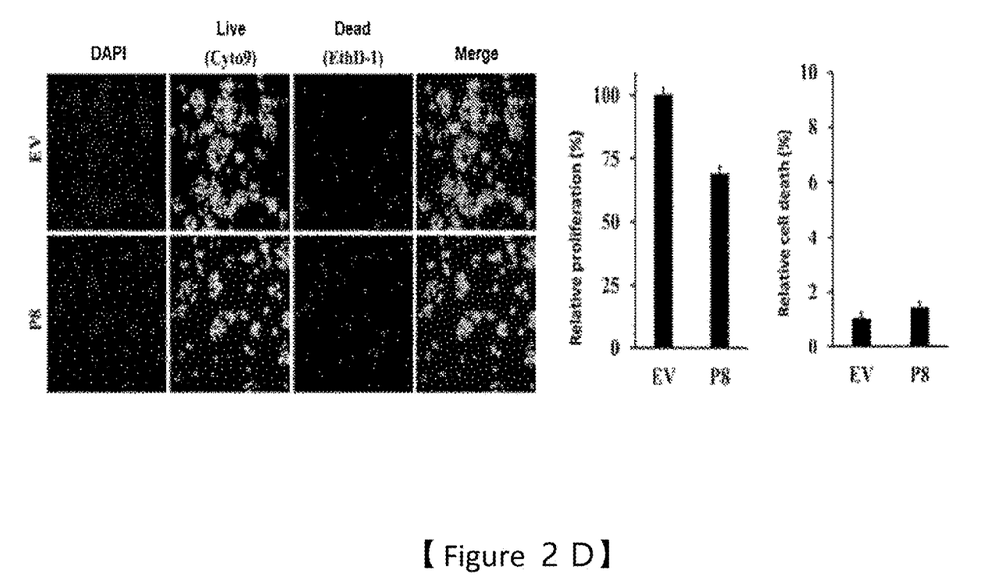
FIG. 2d shows the results of examining anti-cancer efficacy of endogenous expression of P8 protein under an ImageXpress® Micro Confocal microscope. Cells were stained with the live/dead cell markers SYTO™ 9 (green)/EthD-1 (red) or with the total cell marker Hoechst (blue).

To determine the effects of P8 protein on various signaling pathways, the signaling pathways associated with proliferation of susceptible phenotypes were examined First, whether P8 protein induces apoptosis or cell cycle arrest in DLD-1 cells was examined. The number of dead cells after treatment with 40 μM exogenous P8 protein was comparable with that of a control (FIG. 2e). However, the number of dead cells changed after the concentration of exogenous P8 protein treatment was increased. Next, the effect of endogenous P8 protein expression was examined (FIG. 2d). The numbers of dead cells in treated and control groups were similar, suggesting that endogenous P8 protein did not trigger apoptosis.

3. Effects of P8 Protein on Anticancer Signaling Pathways in DLD-1 Cells

Figure 3A:
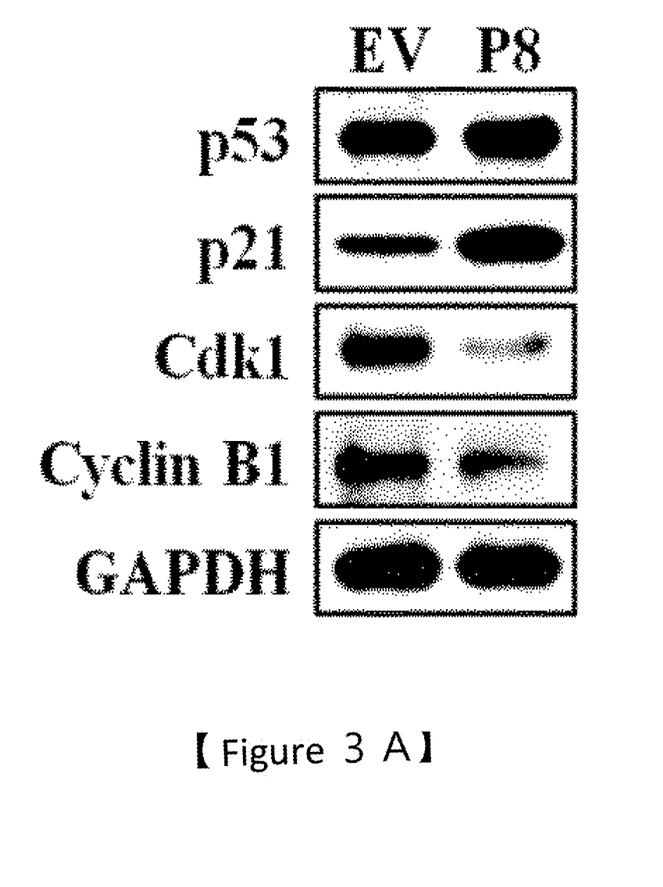
FIG. 3a shows the results of Western blotting that show the effect of endogenous P8 protein expression on molecules associated with G2 arrest in DLD-1 cells (EV, empty vector).
Figure 3B:
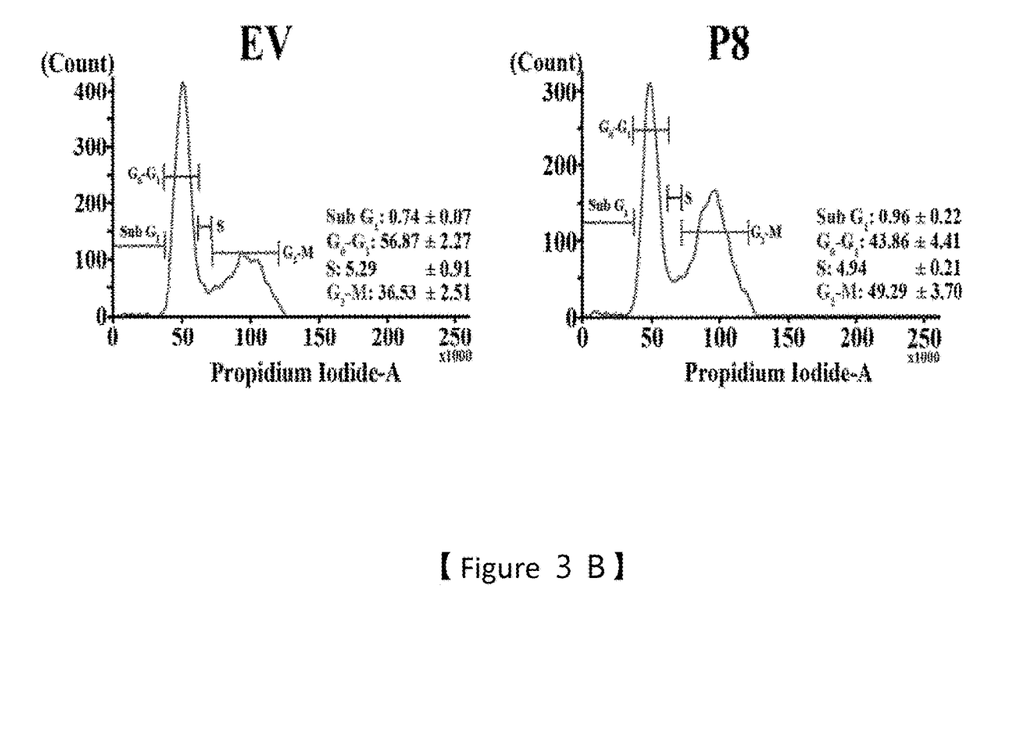
FIG. 3b shows the results of subjecting harvested cells to flow cytometry analysis in order to determine the effects of endogenous P8 protein expression on the cell cycle. Endogenous P8 protein induced arrest of DLD-1 cells at G2 phase.

Next, the present inventors investigated the effects of endogenous P8 protein expression on the cell cycle using Western blotting to detect expression of cell cycle-related proteins (FIG. 3a). It was found that endogenous P8 protein expression strongly reduced expression of both Cyclin B1 and its partner protein Cdk1 in DLD-1 cells. In addition, it was found expression of p21, which suppresses Cyclin B1/Cdk1, significantly increased. It was observed that expression of p53, a positive up-stream regulator of p21, was also induced. These experimental results suggest that endogenous P8 protein might put a brake on the p53-p21 signaling pathway, resulting in arrest of DLD-1 cells at G2. To evaluate the effect of endogenous P8 protein expression on the cell cycle, changes were measured using flow cytometry. Endogenous P8 protein expression induced significant growth arrest at G2 (FIG. 3b).

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereto

INDUSTRIAL APPLICABILITY

The present disclosure relates to a construct for expression of P8 protein derived from lactic acid bacteria, and a composition for treating or preventing colorectal disease containing the same.

The invention claimed is:

1. A P8 protein expression construct comprising: (a) a promoter; and (b) a nucleotide sequence of SEQ ID NO: 3 comprising a P8 protein-encoding nucleotide sequence, wherein the P8 protein-encoding nucleotide sequence is operatively linked to the promoter, wherein the promoter is a promoter for expression in eukaryotic cells, and wherein the P8 protein expression construct expresses P8 protein in mammalian cancer cells.

2. The P8 protein expression construct of claim 1, wherein the expression construct is a plasmid vector- or viral vector-based expression construct.

3. A pharmaceutical composition for treating colorectal disease, the pharmaceutical composition containing: (a) a therapeutically effective amount of the P8 protein expression construct of claim 1; and (b) a pharmaceutically acceptable carrier.

4. The pharmaceutical composition of claim 3, wherein the expression construct is a plasmid vector- or viral vector-based expression construct.

* * * * *

SEQUENCE LISTING

<160> NUMBER OF SEQ ID NOS: 3

<210> SEQ ID NO 1
<211> LENGTH: 222
<212> TYPE: DNA
<213> ORGANISM: Lactobacillus rhamnosus

```
<400> SEQUENCE: 1
atggcaacag tagatcctga aaagacattg tttctcgatg aaccaatgaa caaggtattt      60
gactggagca acagcgaagc acctgtacgt gatgcgctgt gggattatta catggaaaag     120
aacagccgtg ataccatcaa gactgaagaa gaaatgaaac cagtcctaga catgtccgac     180
gatgaggtca aagccctagc agaaaaggtt ctcaagaagt aa                        222

<210> SEQ ID NO 2
<211> LENGTH: 305
<212> TYPE: DNA
<213> ORGANISM: Lactobacillus rhamnosus

<400> SEQUENCE: 2
catatgagag gatcgcatca ccatcaccat cacattacga tatcccaacg accgaaaacc      60
tgtattttca gggatccatg caacagtag atcctgaaaa gacattgttt ctcgatgaac      120
caatgaacaa ggtatttgac tggagcaaca gcgaagcacc tgtccgtgat gcgctgtggg     180
attattacat ggaaaagaac agccgtgata ctatcaagac tgaagaagaa atgaaaccag     240
tcctagacat gtccgacgac gaggtcaaag ccctagcaga aaaggttctc aagaagtagg     300
aattc                                                                 305

<210> SEQ ID NO 3
<211> LENGTH: 236
<212> TYPE: DNA
<213> ORGANISM: Lactobacillus rhamnosus

<400> SEQUENCE: 3
gaattcatgg ctactgtcga cccagaaaaa accctgttct tggacgaacc aatgaataaa      60
gtctttgatt ggtccaactc tgaggccccg gtacgggatg cgttgtggga ttactacatg     120
gaaaaaaatt ccagggatac cattaaaaca gaagaagaaa tgaagccagt tctggacatg     180
agtgacgacg aagtgaaagc cctcgcggaa aaagttctca agaaataggc ggccgc         236
```